United States Patent
Neumann et al.

(10) Patent No.: US 6,723,880 B2
(45) Date of Patent: Apr. 20, 2004

(54) PREPARATION OF SECONDARY AMINES FROM PRIMARY AMINES

(75) Inventors: Peter Neumann, Mannheim (DE); Johann-Peter Melder, Böhl-Iggelheim (DE); Christoph Benisch, Eppelheim (DE); Arthur Höhn, Kirchheim (DE); Joachim Pfeffinger, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/173,774

(22) Filed: Jun. 19, 2002

(65) Prior Publication Data

US 2003/0013873 A1 Jan. 16, 2003

(30) Foreign Application Priority Data

Jun. 21, 2001 (DE) .......................... 101 29 908

(51) Int. Cl.⁷ .................... C07D 417/02; C07D 413/02; C07D 43/02; C07D 41/02
(52) U.S. Cl. ................... 564/469; 564/395; 564/399; 564/474; 564/475; 564/485
(58) Field of Search ................ 564/395, 399, 564/469, 474, 475, 485

(56) References Cited

FOREIGN PATENT DOCUMENTS

DE 30 48 832 9/1981

OTHER PUBLICATIONS

Database CAPLUS on STN, Acc. No. 1991:408080, Kaesbauer et al., EP 424764 (abstract).*
Database CAPLUS on STN, Acc. No. 1979:523393, Knofe et al., DD 133229 (abstract).*

Derwent Abst. DE 3048–832 (1981).

* cited by examiner

Primary Examiner—Brian Davis
(74) Attorney, Agent, or Firm—Keil & Weinkauf

(57) ABSTRACT

A process for producing secondary amines of the formula $R^1R^2N-A-NH-A-NR^1R^2$, where $R^1$ and $R^2$ are linear or branched $C_{1-20}$-alkyl radicals, optionally substituted with from 1 to 5 phenyl groups; or cyclohexyl radicals; or together with the nitrogen atom to which they are bound, form a 3 to 7 membered saturated ring, optionally containing further hetero atoms selected from the group consisting of N, O and S, and optionally substituted with from 1 to 5 $C_{1-2}$-alkyl groups. The group A is a linear or branched $C_{2-20}$-alkylene group, optionally containing from 1 to 5 phenylene groups; or a radical of the formula $-CH(R^3)-[CH_2]_k-X-[CH(R^3)-[CH_2]_k-X]_m-CH(R^3)-[CH_2]_k-$, where $R^3$ is H or $CH_3$, X is O, S or $NR^4$, $R^4$ is H or a linear or branched $C_{1-4}$-alkyl group, k is 1 or 2, and m is an integer from 0 to 4; or a group of the formula

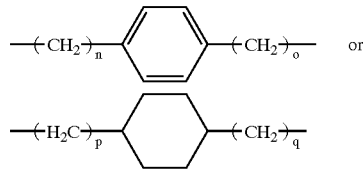

where n, o, p, and q are, independently, integers from 1 to 4. In this process, primary amines of the formula $R^1R^2N-A-NH_2$ are reacted in the presence of hydrogen and a catalyst comprising at least one element or compound of an element of groups VIII and IB of the Periodic Table, preferably group IB, and in particular, Cu. Through this process, a high selectivity of the desired amines can be achieved.

26 Claims, No Drawings

PREPARATION OF SECONDARY AMINES FROM PRIMARY AMINES

The present invention relates to a process for preparing secondary amines from primary amines over transition metal catalysts.

Processes for preparing secondary amines from primary amines are known per se. It is prior art to convert a primary amine having the desired substituents or structural elements into the desired secondary amine under hydrogen and under the reaction conditions chosen in each case. Various catalysts are used; the pressures and temperatures employed in the reaction vary widely. A frequent problem in this synthesis of the secondary amines is that the conversion or the selectivity to the desired product frequently do not achieve the desired values. It is often also necessary to use expensive noble metal catalysts.

DE-A 30 48 832 relates to a process for preparing amines, in particular bis(3-dimethylamino)propylamine (bis-DMAPA) from 3-dimethylaminopropionitrile (DMAPN) or 3-dimethylaminopropylamine (DMAPA) or mixtures of DMAPN and DMAPA. In an example, a bis-DMAPA selectivity of 80% is achieved at a DMAPA conversion of 53% at high pressure (173 bar) over Ni—Cu—$Cr_2O_3$, while a bis-DMAPA selectivity of 88% is achieved at a DMAPA conversion of 49% over Co—Cu—$Cr_2O_3$.

It is found here that, in particular, the conversions are much too low. In addition, for environmental reasons, the use of chromium-containing catalysts is no longer acceptable.

It is an object of the present invention to provide a process for preparing secondary amines from primary amines which can be carried out using chromium-free catalysts and gives the desired secondary amines in high yields and selectivities.

We have found that this object is achieved by a process for preparing a secondary amine of the formula $$R^1R^2N—A—\underset{H}{N}—A—NR^1R^2 \quad (I)$$

where
  $R^1$, $R^2$ may be identical or different and are each, independently of one another, a linear or branched alkyl radical having from 1 to 20 carbon atoms which may bear from 1 to 5 phenyl groups as substituents or a cyclohexyl radical or together with the N atom to which they are bound form a 3- to 7-membered saturated ring which may contain further heteroatoms selected from the group consisting of N, O and S and may be substituted by from 1 to 5 alkyl groups having 1 or 2 carbon atoms,
  A is a linear or branched alkylene group having from 2 to 20 carbon atoms which may have from 1 to 5 phenylene groups in its chain, or a radical of the formula (B)

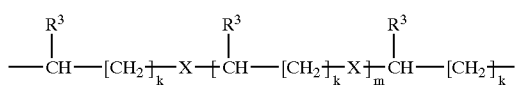

where $R^3$=H or $CH_3$, X=O or S or an $NR^4$ group in which $R^4$ is H or a linear or branched alkyl group having from 1 to 4 carbon atoms, k is 1 or 2 and m is an integer from 0 to 4, or a group of the formula

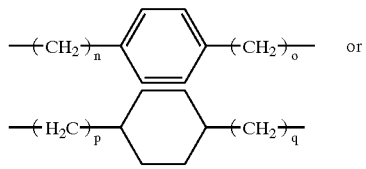

where n, o and p, q are each, independently of one another, integers from 1 to 4,
by reaction of primary amines of the formula $$R^1R^2N—A—NH_2 \quad (II),$$

where $R^1$, $R^2$ and A are as defined for formula (I), in the presence of hydrogen and a catalyst comprising at least one element or compound of an element of groups VIII and IB of the Periodic Table of the Elements. In one embodiment of the present invention, the catalyst composition can be free of a metal of group IB or a compound thereof. In a preferred embodiment, the catalyst contains up to 50% by weight of at least one element or compound of an element of group IB of the Periodic Table of the Elements.

The catalysts used in the process of the present invention thus comprise, in the active catalyst composition, up to 100% by weight of at least one element or at least one compound of an element of groups VIII and IB of the Periodic Table of the Elements, i.e. from the group consisting of Fe, Ru, Os, Co, Rh, Ir, Ni, Pd, Pt, Cu, Ag and Au. In one embodiment, the active catalyst composition can contain 0% by weight, in a preferred embodiment up to 50% by weight, or at least one element or at least one compound of an element of group IB of the Periodic Table of the Elements, i.e. from the group consisting of Cu, Ag and Au, preferably Cu. The amount of metal or compound of a metal of group IB is, in a more preferred embodiment, from 1 to 30% by weight, in particular from 10 to 25% by weight, based on the total amount of active catalyst composition. In a further preferred embodiment, the active catalyst composition comprises at least one element or at least one compound of an element from the group consisting of Ni, Co, Cu, Ru, Rh, Ir, Pd, Pt, in the ratios indicated above for the general and preferred embodiments.

If compounds of the specified metals are used for preparing the catalyst, it is possible to use, for example, the oxides, nitrates, carbonates, chlorides and acetates.

In the most preferred embodiment of the present invention, the oxides of the elements employed are used for preparing the catalyst. These are then reduced before use in the reaction, preferably by treatment with hydrogen. This gives a catalyst in which the metal components employed are present in elemental, finely-divided form.

The catalysts can be used as all-active catalysts or in supported form. When using supported catalysts, the proportion of support is from 10 to 90% by weight, based on the total mass of the catalyst (active composition plus support).

As supports, it is possible to use all known suitable supports, for example, activated carbon, silicon carbide or metal oxides. The use of metal oxides is preferred. Among metal oxides, preference is given to using aluminum oxide, silicon dioxide, titanium dioxide, zirconium dioxide, zinc oxide, magnesium oxide or mixtures thereof, which may, if appropriate, be doped with alkali metal oxides and/or alkaline earth metal oxides. Particular preference is given to γ-aluminum oxide, silicon dioxide, zirconium dioxide or titanium dioxide or mixtures thereof, in particular $Al_2O_3$. The supports can be used in any form, for example as extrudates (rod form), pellets, tablets, monoliths, woven meshes, knitteds or in powder form. The supported catalysts can be prepared by generally known methods. These include, for instance, impregnation of a support with solutions of compounds of the metal components used. Suitable solvents include all customary solvents, for instance water, methanol, ethanol or acetone; preference is given to using water. Furthermore, the catalyst can be prepared by coprecipitation or sequential precipitation of the catalyst components, followed by filtration and washing of the filter cake. The impregnation or precipitation is followed by a drying step (50–200° C.) and a calcination step (200–500° C.). The catalysts are then reduced at final temperatures of from 200 to 400° C. and can subsequently be passivated, since the reduced metals are pyrophoric. After installation of the catalysts in the synthesis reactor, the catalysts can be reactivated by reduction with hydrogen at from 100 to 300° C. before the reaction is started.

According to the present invention, preference is given to the use as starting materials of primary amines of the formula (I) and the synthesis of secondary amines of the formula (II) in which the substituents $R^1$, $R^2$ and A have the following meanings:

A is a linear or branched methylene chain having from 2 to 10 carbon atoms or a group of the formula

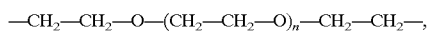

where n is an integer from 0 to 2, $R^1$, $R^2$ are identical or different and are each, independently of one another, an alkyl radical having from 1 to 12 carbon atoms or together with the nitrogen atom to which they are bound form a 5- or 6-membered saturated ring which may contain a further heteroatom selected from the group consisting of O and N.

Particular preference is given to amines of the formulae (I) and (II) in which

A is an alkylene group having from 1 to 6 carbon atoms or a group of the formula

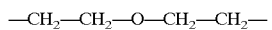

and $R^1$ and $R^2$ may be identical or different and are each, independently of one another, a linear or branched alkyl radical having from 1 to 4 carbon atoms or together with the nitrogen atom to which they are bound form a piperidine ring or a morpholine ring.

In particular, 3-dimethylaminopropylamine (DMAPA) is used to produce bis-3-dimethylaminopropylamine (bis-DMAPA).

The process of the present invention is carried out at from 50 to 250° C., preferably from 90° C. to 170° C., particularly preferably from 120° C. to 160° C., at pressures of from 5 to 350 bar, preferably from 5 to 200 bar, particularly preferably from 10 to 100 bar, in particular from 10 to 30 bar, either batchwise or preferably continuously in pressure apparatuses such as autoclaves or preferably in a tube reactor. The pressure is preferably the hydrogen pressure in the reactor. When using a tube reactor, the catalyst used can also be present as a fixed-bed catalyst.

The reaction can be carried out in the gas phase or in the liquid phase.

The space velocity over the catalyst, based on the primary amine used, is preferably from 0.1 to 2 kg $l^{-1}h^{-1}$, in particular from 0.8 to 1.2 kg $l^{-1}h^{-1}$. Part of the liquid reaction product can be recirculated to the reaction.

The process of the present invention can be carried out in the absence of solvents or in solvents such as water, methanol, ethanol, tetrahydrofuran, methyl tert-butyl ether or N-methylpyrrolidone. If a solvent is used, the primary amine employed can be dissolved in the solvent. The solvent can also be fed separately into the reactor at any point. Preference is given to carrying out the process in the absence of a solvent.

The desired secondary amine obtained by means of the process of the present invention can be separated off from the reaction mixture and purified in a manner known per se, for example by distillation.

It is also possible, for example, to obtain a stream comprising pure secondary amine and a stream comprising primary amine by rectification and to recirculate the stream comprising the primary amine to the synthesis.

According to the present invention, the primary amines of the formula (II) and the secondary amines of the formula (I) are preferably obtained in a weight ratio of from 10:1 to 1:10, preferably 2:3–4.

The process of the present invention makes it possible to obtain end product mixtures which contain only small amounts of tertiary amines, generally in amounts of <10% by weight. The process can also be carried out so that <5% by weight of tertiary amines are obtained. Under optimum reaction conditions, it is also possible for no tertiary amines to be formed.

The amines obtainable by means of the process of the present invention, preferably bis-DMAPA, are hardeners for epoxy resins, catalysts for polyurethanes, intermediates for the preparation of quaternary ammonium compounds, plasticizers, corrosion inhibitors, textile assistants, dyes and emulsifiers. Polyfunctional tertiary amines are also employed for producing synthetic resins, ion exchangers, pharmaceuticals, crop protection agents and pesticides.

The invention is illustrated by the following example:

EXAMPLE

A heated tube reactor which has an internal diameter of 10 mm and a total length of 35 cm and is provided with a centrally located thermocouple is charged with 89 g of the catalyst. The catalyst comprises 42% by weight of CoO, 42% by weight of NiO and 16% by weight of CuO on an aluminum oxide support (76% by weight of the total mass of the catalyst).

Prior to the reaction, the catalyst was activated at 180° C., firstly in a stream of nitrogen and hydrogen in a ratio of 4:1, subsequently in a stream of nitrogen and hydrogen in a ratio of 1:1 and finally in pure hydrogen.

1200 g/(1 *h) of 3-dimethylaminopropylamine (DMAPA) and 20 standard 1/h of hydrogen were passed through the reactor from the bottom upward. The reactor is maintained at 140° C. and a total pressure of 30 bar.

The mixture leaving the reactor was cooled and depressurized to atmospheric pressure. By means of gas-chromatographic analysis, the output from the reactor was found to comprise 52% by weight of bis-(3-dimethylaminopropyl)amine (bis-DMAPA), 42% by weight of 3-dimethylaminopropylamine (DMAPA) and 6% by weight of various by-products. The DMAPA conversion was thus 58%, and the selectivity to bis-DMAPA was 90%.

300 g of the liquid output from the reactor were subsequently distilled batchwise under reduced pressure at a reflux ratio of 5:1 in a laboratory distillation apparatus provided with packing (10 theoretical plates). This gave 157 g of a fraction containing 97.4% by weight of DMAPA and 129 g of a second fraction containing 98.4% by weight of bis-DMAPA.

We claim:

1. A process for preparing a secondary amine of the formula $$R^1R^2N-A-NH-A-NR^1R^2 \quad (I)$$

where

R$^1$, R$^2$ may be identical or different and are each, independently of one another, a linear or branched alkyl radical having from 1 to 20 carbon atoms which may bear from 1 to 5 phenyl groups as substituents or a cyclohexyl radical or together with the N atom to which they are bound form a 3- to 7-membered saturated ring which may contain further heteroatoms selected from the group consisting of N, O and S and may be substituted by from 1 to 5 alkyl groups having 1 or 2 carbon atoms, A is a linear or branched alkylene group having from 2 to 20 carbon atoms which may have from 1 to 5 phenylene groups in its chain, or a radical of the formula

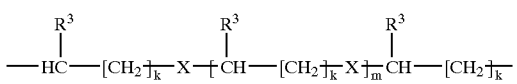

(B)

where R$^3$=H or CH$_3$, X=O or S or an NR$^4$ group in which R$^4$ is H or a linear or branched alkyl group having from 1 to 4 carbon atoms, k is 1 or 2 and m is an integer from 0 to 4, or a group of the formula

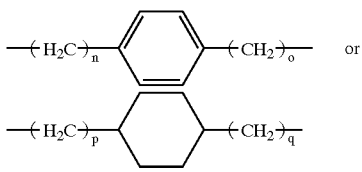

where n, o and p, q are each, independently of one another, integers from 1 to 4, by reaction of primary amines of the formula $$R^1R^2N-A-NH_2 \quad (II),$$

where R$^1$, R$^2$ and A are as defined for formula (I), in the presence of hydrogen and a chromium-free catalyst comprising at least one element or compound of an element of groups VIII and IB of the Periodic Table of the Elements.

2. A process as claimed in claim 1, wherein the substituents R$^1$, R$^2$ and A in the amines (I) and (II) have the following meanings:

A is a linear or branched methylene chain having from 2 to 10 carbon atoms or a group of the formula $$-CH_2-CH_2-O-(CH_2-CH_2-O)_n-CH_2-CH_2-,$$

where n is an integer from 0 to 2,

R$^1$, R$^2$ are identical or different and are each, independently of one another, an alkyl radical having from 1 to 12 carbon atoms or together with the nitrogen atom to which they are bound form a 5- or 6-membered saturated ring which may contain a further heteroatom selected from the group consisting of O and N.

3. A process as claimed in claim 2, wherein, in the amines (I) and (II),

A is an alkylene group having from 1 to 6 carbon atoms or a group of the formula $$-CH_2-CH_2-O-CH_2-CH_2-$$

and

R$^1$ and R$^2$ may be identical or different and are each, independently of one another, a linear or branched alkyl radical having from 1 to 4 carbon atoms or together with the nitrogen atom to which they are bound form a piperidine ring or a morpholine ring.

4. A process as claimed in claim 3, wherein 3-dimethylaminopropylamine is converted into bis-3-dimethylaminopropylamine.

5. A process as claimed in claim 1, wherein the catalyst comprises, in the active composition, 0% by weight of a metal or compound of a metal of group IB of the Periodic Table of the Elements, based on the total amount of active catalyst composition.

6. A process as claimed in claim 1, wherein the catalyst comprises, in the active composition, up to 50% by weight of a metal or a compound of group IB of the Periodic Table of the Elements.

7. A process as claimed in claim 6, wherein the catalyst comprises, in the active composition, from 1 to 30% by weight of a metal or a compound of group IB of the Periodic Table of the Elements.

8. A process as claimed in claim 6, wherein the catalyst comprises, in the active composition, from 10 to 25% by weight of a metal or a compound of group IB of the Periodic Table of the Elements.

9. A process as claimed in claim 1, wherein the catalyst comprises, in the active composition, at least one element or at least one compound of an element from the group consisting of Ni, Co, Cu, Ru, Rh, Ir, Pd, Pt.

10. A process as claimed in claim 1, wherein the catalyst has been applied to a suitable support.

11. A process as claimed in claim 10, wherein the catalyst has been applied to a support comprising activated carbon, silicon carbide, metal oxides or mixtures thereof.

12. A process as claimed in claim 11, wherein the catalyst has been applied to a support comprising aluminum oxide, silicon dioxide, titanium dioxide, zirconium dioxide, zinc oxide, magnesium oxide or mixtures thereof in particular γ-aluminum oxide, silicon dioxide, zirconium dioxide, titanium dioxide or mixtures thereof.

13. A process as claimed in claim 10, wherein the support makes up from 10 to 90% by weight of the total mass of the catalyst.

14. A process as claimed in claim 1 carried out at from 50 to 250° C.

15. A process as claimed in claim 14, wherein the process is carried out at from 90 to 170° C.

16. A process as claimed in claim 15, wherein the process is carried out at from 120 to 160° C.

17. A process as claimed in claim 1, wherein the process is carried out at from 5 to 350 bar.

18. A process as claimed in claim 17, wherein the process is carried out at from 5 to 200 bar.

19. A process as claimed in claim 18, wherein the process is carried out at from 10 to 100 bar.

20. A process as claimed in claim 19, wherein the process is carried out at from 10 to 30 bar.

21. A process as claimed in claim 1 carried out at a space velocity over the catalyst of from 0.1 to 2 kg l$^{-1}$ h$^{-1}$, based on the primary amine.

22. A process as claimed in claim 21 carried out at a space velocity over the catalyst of from 0.8 to 1.2 kg $l^{-1}$ $h^{-1}$.

23. A process as claimed in claim 1 carried out batchwise or continuously.

24. A process as claimed in claim 23 carried out continuously.

25. A process as claimed in claim 24 carried out in a tube reactor.

26. A process for preparing a secondary amine of the formula $$R^1R^2N\text{---}A\text{---}NH\text{---}A\text{---}NR^1R^2 \quad (I)$$

where

R$^1$, R$^2$ may be identical or different and are each, independently of one another a linear or branched alkyl radical having from 1 to 20 carbon atoms which may bear from 1 to 5 phenyl groups as substituents or a cyclohexyl radical or together with the N atom to which they are bound form a 3- to 7-membered saturated ring which may contain further heteroatoms selected from the group consisting of N, O and S and may be substituted by from 1 to 5 alkyl groups having 1 or 2 carbon atoms, A is a linear or branched alkylene group having from 2 to 20 carbon atoms which may have from 1 to 5 phenylene groups in its chain, or a radical of the formula

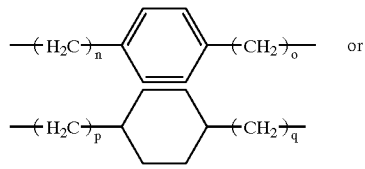
(B)

where R$^3$=H or CH$_3$, X=O or S or an NR$^4$ group in which R$^4$ is H or a linear or branched alkyl group having from 1 to 4 carbon atoms, k is 1 or 2 and m is an integer from 0 to 4, or a group of the formula

where n, o and p, q are each, independently of one another, integers from 1 to 4, by reaction of primary amines of the formula $$R^1R^2N\text{---}A\text{---}NH_2 \quad (II),$$

where R$^1$, R$^2$ and A are as defined for formula (I), in the presence of hydrogen and a chromium-free catalyst comprising from 1 to 30% by weight of a metal or a compound of group IB, and at least one element or at least one compound of an element selected from the group consisting of Ni, Co, Ru, Rh, Ir, Pd, Pt.

* * * * *